(12) United States Patent
Barguirdjian et al.

(10) Patent No.: US 6,802,205 B2
(45) Date of Patent: Oct. 12, 2004

(54) MOISTURE DETECTION SYSTEM AND METHOD OF USE THEREOF

(75) Inventors: Pascal Barguirdjian, Saint Malo (FR); Michel Haigron, Saint Malo (FR); Allan Rex Hawk, Cheswick, PA (US); Kwaku Koi Koram, Wexford, PA (US)

(73) Assignee: PPG Industries Ohio, Inc., Cleveland, OH (US)

(*) Notice: Subject to any disclaimer, the term of this patent is extended or adjusted under 35 U.S.C. 154(b) by 0 days.

(21) Appl. No.: 10/308,670

(22) Filed: Dec. 3, 2002

(65) Prior Publication Data

US 2003/0159504 A1 Aug. 28, 2003

Related U.S. Application Data

(63) Continuation-in-part of application No. PCT/US02/06163, filed on Feb. 28, 2002.

(51) Int. Cl.[7] ................................................. G01N 5/02
(52) U.S. Cl. ............................. 73/73; 73/74; 318/443; 318/444; 318/448
(58) Field of Search ................. 73/73, 74; 318/443–448

(56) References Cited

U.S. PATENT DOCUMENTS

| | | | |
|---|---|---|---|
| 3,826,979 A | 7/1974 | Steinmann | 324/61 R |
| 4,428,232 A | 1/1984 | Tanaka et al. | 73/304 C |
| 4,703,237 A | 10/1987 | Hochstein | 318/483 |
| 4,748,390 A | 5/1988 | Okushima et al. | 318/483 |
| 5,598,146 A | 1/1997 | Schroder | 340/602 |
| 5,602,333 A | 2/1997 | Larrabee et al. | 73/149 |
| 5,659,294 A | 8/1997 | Schroder | 340/602 |
| 5,661,303 A | 8/1997 | Teder | 250/341.8 |
| 5,668,478 A | 9/1997 | Buschur | 324/690 |
| 5,672,976 A | 9/1997 | Egger et al. | 324/668 |
| 5,682,788 A | 11/1997 | Netzer | 73/73 |
| 5,694,012 A | 12/1997 | Pientka et al. | 318/444 |
| 5,703,568 A | 12/1997 | Hegyi | 340/602 |
| 5,780,718 A | 7/1998 | Weber | 73/29.01 |
| 5,780,719 A | 7/1998 | VanDam | 73/29.01 |
| 5,783,743 A | 7/1998 | Weber | 73/29.01 |

(List continued on next page.)

FOREIGN PATENT DOCUMENTS

| | | |
|---|---|---|
| AU | 6895194 | 2/1995 |
| DE | 101 27 978 | 11/2002 |
| DE | 101 27 990 | 12/2002 |
| DE | 101 28 010 | 1/2003 |
| EP | 0 308 990 | 3/1989 |
| EP | 0 638 822 | 2/1995 |
| EP | 1 264 746 | 5/2002 |

OTHER PUBLICATIONS

U.S. patent application Publication No. US 2002/0189329 A1 published Dec. 19, 2002.
PCT Application Ser. No. PCT/US02/06163 filed Feb. 28, 2002.

*Primary Examiner*—Edward Lefkowitz
*Assistant Examiner*—Alandra Ellington
(74) *Attorney, Agent, or Firm*—Andrew C. Siminerio

(57) ABSTRACT

A moisture detection system includes an electrical conductor disposed on a surface of a substrate. The electrical conductor has a resonant frequency that varies as a function of an amount of moisture present adjacent the electrical conductor. An oscillator outputs an oscillator signal at a predetermined amplitude and a predetermined frequency. A resonator circuit is coupled to the electrical conductor and is responsive to the oscillator signal and the resonant frequency of the electrical conductor for outputting a resonator signal having an amplitude related to the resonant frequency of the electrical conductor. A filter circuit rectifies and filters the resonator signal and provides it to an analog-to-digital converter which outputs a digital signal related to the rectified and filtered resonator signal. A controller is responsive to the digital signal for causing a system associated with the substrate to operate in accordance with the digital signal.

38 Claims, 5 Drawing Sheets

U.S. PATENT DOCUMENTS

| | | | |
|---|---|---|---|
| 5,801,307 A | 9/1998 | Netzer | 73/170.17 |
| 5,818,341 A | 10/1998 | Saurer et al. | 340/602 |
| 5,900,821 A | 5/1999 | Petzold | 340/604 |
| 5,990,647 A | 11/1999 | Zettler | 318/483 |
| 6,052,196 A | 4/2000 | Pientka et al. | 356/445 |
| 6,066,933 A | 5/2000 | Ponziana | 318/483 |
| 6,084,519 A | 7/2000 | Coulling et al. | 340/602 |
| 6,094,981 A | 8/2000 | Hochstein | 73/170.17 |
| 6,118,383 A | 9/2000 | Hegyi | 340/602 |
| 6,207,967 B1 | 3/2001 | Hochstein | 250/574 |
| 6,218,741 B1 | 4/2001 | Braun et al. | 307/10.1 |
| 6,232,603 B1 | 5/2001 | Nelson | 250/339.11 |
| 6,250,148 B1 | 6/2001 | Lynam | 73/270.17 |
| 6,262,407 B1 | 7/2001 | Teder | 250/205 |
| 6,262,410 B1 | 7/2001 | Stam et al. | 250/208.1 |
| 6,268,612 B1 | 7/2001 | Teder | 250/574 |
| 6,313,457 B1 | 11/2001 | Bauer et al. | 250/214 C |

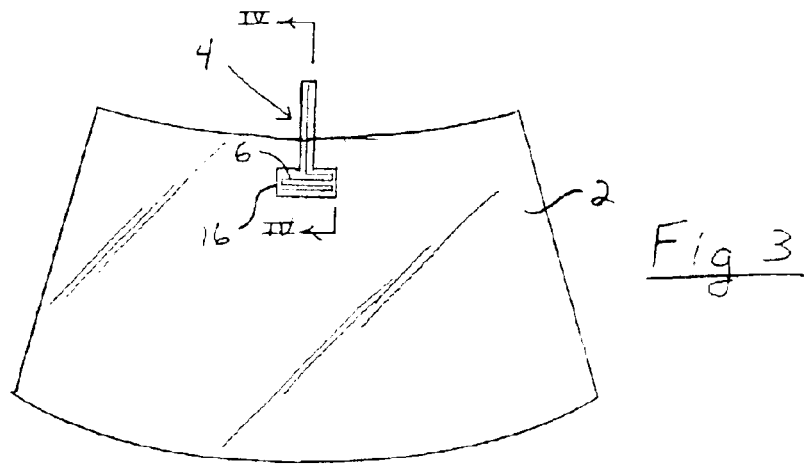
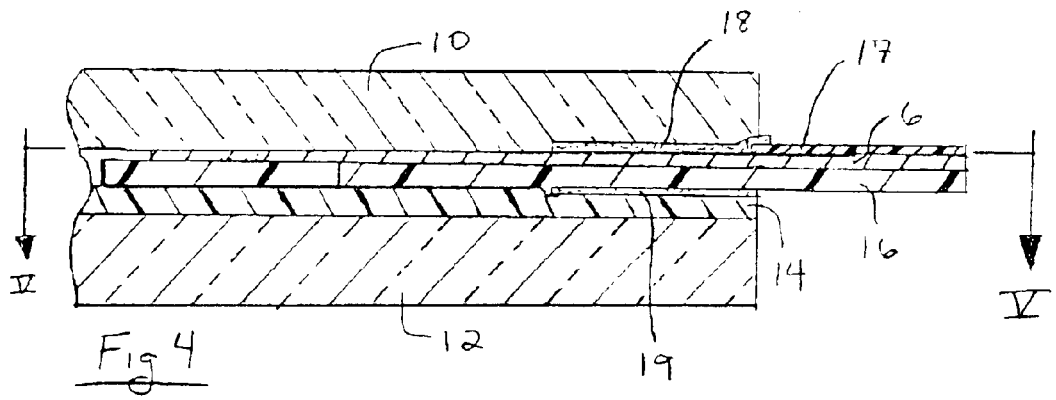
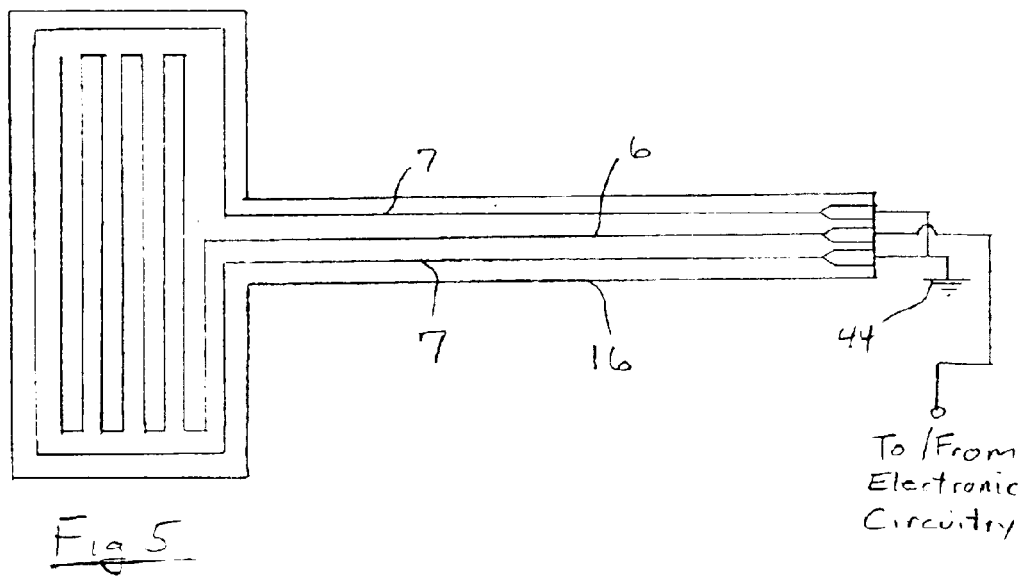

MOISTURE DETECTION SYSTEM AND METHOD OF USE THEREOF

CROSS REFERENCE TO RELATED APPLICATION

This application is a continuation-in-part of International Application Ser. No. PCT/US02/06163, filed Feb. 28, 2002.

BACKGROUND OF THE INVENTION

1. Field of the Invention

The present invention relates to moisture detection and, more particularly, to moisture detection on a vehicle windshield.

2. Description of the Prior Art

Heretofore, the detection of moisture on a windshield of a vehicle was accomplished in four basic manners. Namely, capacitive sensor systems, resistive sensor systems, ultrasonic sensor systems and optical sensor systems.

A capacitive sensor system includes a capacitor formed on the windshield. In response to moisture on the windshield, the capacitance of the capacitor changes. A sensing circuit is connected to detect the changing capacitance and to control the operation of a windshield wiper as a function of the changing capacitance. Examples of capacitive moisture sensors include U.S. Pat. No. 5,668,478 to Buschur; U.S. Pat. No. 5,682,788 to Netzer; U.S. Pat. No. 5,801,307 to Netzer; and U.S. Pat. No. 6,094,981 to Hochstein.

A resistive measurement system includes two conductive elements disposed in spaced relation on the windshield, or another part of the vehicle, such as a conventional whip antenna. Circuitry coupled to the conductive elements measures a change in resistance thereof in response to water bridging the resistive elements and controls the operation of the windshield wiper as a function of the change in resistance. Examples of resistive measurement systems include U.S. Pat. No. 5,659,294 to Schroder; U.S. Pat. No. 5,598,146 to Schroder; U.S. Pat. No. 5,780,718 to Weber; U.S. Pat. No. 5,780,719 to VanDam; U.S. Pat. No. 5,783,743 to Weber; and U.S. Pat. No. 5,900,821 to Petzold.

An ultrasonic sensor system includes a transducer which emits an ultrasonic signal toward a first face of a sheet and receives a reflected ultrasonic signal on a second face of the sheet. The variation in the reflected signal is utilized to determine the presence or absence of foreign bodies on the second face of the sheet. Examples of ultrasonic sensor systems include U.S. Pat. No. 5,818,341 to Saurer et al. and European Publication No. EP 0638822.

An optical sensor system includes a light detector positioned to detect light reflected off a windshield from a light source. In response to the presence of moisture on the windshield, the amount of light detected by the light sensor will change due to changing reflection of the light from the light source, thus causing a change in the output of the light sensor. Detecting circuitry detects the change in output from the light detector in response to the change in light impinging thereon and operates the windshield wiper as a function of the change. Examples of light detecting systems include U.S. Pat. No. 5,694,012 to Pientka et al.; U.S. Pat. No. 5,990,647 to Zettler; U.S. Pat. No. 6,052,196 to Pientka et al.; U.S. Pat. No. 6,066,933 to Ponziana; U.S. Pat. No. 6,084,519 to Coulling et al.; U.S. Pat. No. 6,207,967 to Hochstein; U.S. Pat. No. 5,661,303 to Teder; U.S. Pat. No. 6,250,148 to Lynam; U.S. Pat. No. 6,218,741 to Braun et al.; and U.S. Pat. No. 6,232,603 to Nelson.

A problem with a capacitive sensor system includes the need to form a capacitor having sufficient capacitance whereupon the change in capacitance in response to the presence of rain on the windshield can be detected by suitable detection circuitry. Another problem with a capacitive sensor system is the change in capacitance due to heating or cooling of the metal films forming the capacitor thereby resulting in a change in the capacitance of the capacitor during use.

A problem with a resistive sensor system includes the need to have the resistive elements formed on the outer surface of the windshield whereupon the resistive elements are exposed to weather and possible deterioration. In addition, the resistive elements of a resistive sensor system are also subject to changes in resistance due to changes in the temperature.

A problem with an ultrasonic sensor system and an optical sensor system includes the need to position the transducer of the ultrasonic sensor system and the light transmitter and light receiver of the optical sensor system inside the vehicle to detect the presence of moisture at a suitable location on the windshield. However, positioning the ultrasonic sensor system or the optical sensor system at a suitable location on the windshield often results in partially blocking a driver's view through the windshield or in the positioning of such sensor system at less than an optimal location for detecting the presence of moisture on the windshield. Moreover, the sensitivity of an optical sensor to detect moisture can be compromised by the color or shade of the windshield in the path of the light propagating from the light transmitter to the light receiver.

It is, therefore, desirable to overcome the above problems and others by providing a moisture detection system having a small, nearly invisible, sensor disposed on a flexible substrate that is coupled to a sheet, such as a windshield, circuitry for stimulating the sensor, and detection circuitry for detecting a change in the resonant frequency of the sensor due to the presence of moisture on the sheet and, more particularly, the amount or rate of accumulation of moisture on the sheet. It is also desirable to provide a method for detecting the presence of moisture on a sheet by detecting a change in the resonant frequency of a sensor that is disposed on a flexible substrate that is coupled to the sheet. Still other desirable apparatus and methods may become apparent to those of ordinary skill in the art upon reading and understanding the following detailed description.

SUMMARY OF THE INVENTION

The invention is a moisture detection system that includes an electrical conductor disposed on a surface of a substrate. The electrical conductor has a resonant frequency that varies as a function of an amount of moisture present adjacent the electrical conductor. An oscillator outputs an oscillator signal at a predetermined amplitude and a predetermined frequency. A resonator circuit is coupled to the electrical conductor and is responsive to the oscillator signal for outputting a resonator signal having an amplitude related to the resonant frequency of the electrical conductor. A filter circuit is responsive to the resonator signal for outputting a rectified and filtered signal. An analog-to-digital converter is responsive to the rectified and filtered signal for outputting a digital signal related to the rectified and filtered signal. A controller is responsive to the digital signal for causing another system to operate in accordance with the digital signal.

The other system can be a wiper system that is responsive to the controller for adjusting a rate moisture is removed from adjacent the electrical conductor as a function of an amount of moisture present adjacent the electrical conductor and/or a rate moisture accumulates adjacent the electrical conductor.

The substrate can be a vehicle windshield having a plurality of transparent sheets laminated together. The electrical conductor can be sandwiched between the transparent sheets.

The substrate can be a flexible substrate. The moisture detection system can include a vehicle windshield having a plurality of transparent sheets laminated together with the flexible substrate sandwiched therebetween. The flexible substrate can include a ground conductor disposed on the flexible substrate at least partially surrounding the electrical conductor. The flexible substrate can include also or alternatively a conductive material disposed on a surface thereof opposite the electrical conductor. The conductive material can have a form that defines a faraday shield. Still further, an electrically conductive coating can also or alternatively be provided on a surface of at least one transparent sheet positioned on a side of the flexible substrate opposite an exterior surface of the vehicle windshield.

The resonator circuit can include a tank circuit having a capacitor and inductor connected in parallel between the electrical conductor and a reference voltage, and a resistor connected between the oscillator and the electrical conductor side of the tank circuit. The filter circuit can include a diode connected to conduct current from the resonator toward the analog-to-digital converter and a capacitor connected between an end of the diode adjacent the analog-to-digital converter and the reference voltage.

The invention is also a moisture detection system that includes means disposed on a substrate for conducting electrical current. The conducting means has a resonant frequency that changes as a function of moisture present adjacent the conducting means. An oscillator outputs to the conducting means an oscillator signal having a desired frequency and a first amplitude. A means responsive to the oscillator signal outputs a resonator signal having a second amplitude related to the resonant frequency of the conducting means. The second amplitude can be greater than or less than the first amplitude. The moisture detection system also includes means responsive to the resonator signal for outputting a control signal having a value related to the second amplitude.

The moisture detection system can include a wiper system disposed in operative relation to the sheet. The wiper system is responsive to the control signal for wiping moisture from adjacent the conducting means based on an amount of moisture on the sheet and/or a rate moisture accumulates adjacent the conducting means.

The conducting means can include one or more lines of conductive material, one or more sheets of conductive material, or a dispersion of conductive particles in the form of one or more lines and/or sheets.

The substrate can be a windshield that includes plural sheets of glass laminated together. The conducting means can be sandwiched between the sheets of glass.

The substrate can be a flexible substrate that is coupled to a sheet. The conducting means has a resonant frequency that changes as a function of moisture on the sheet. A wiper system can be disposed in operative relation to the sheet and responsive to the control signal for wiping the sheet based on an amount of moisture on the sheet and/or a rate moisture accumulates on the sheet.

The conducting means can include one or more lines of electrically conductive material disposed on the flexible substrate.

The sheet can be a windshield that includes plural sheets of glass laminated together. The flexible substrate can be sandwiched between the sheets of glass.

The flexible substrate can include a ground conductor disposed thereon at least partially surrounding the conducting means or a conductive material disposed on a surface of the flexible substrate opposite the conducting means, with said conductive material having a form that defines a faraday shield. An electrically conductive coating can also be disposed on a surface of at least one sheet.

Still further, the invention is a method of moisture detection. The method includes providing a substrate having an electrical conductor disposed thereon. The electrical conductor is stimulated with an oscillator signal in the absence of moisture adjacent the electrical conductor. A first amplitude of the response of the electrical conductor to this stimulation is determined. The electrical conductor is stimulated with the oscillator signal when moisture is present adjacent the electrical conductor. A second amplitude of the response of the electrical conductor to this stimulation is determined. The second amplitude is different than the first amplitude due to a change in the resonant frequency of the electrical conductor in response to the presence of moisture adjacent the electrical conductor. A difference is determined between the first amplitude and the second amplitude, wherein the difference is related to the amount of moisture present adjacent the electrical conductor.

The method can also include removing moisture from adjacent the electrical conductor at a rate related to the difference.

The substrate can be sandwiched between at least two sheets of glass. A shielding means can be provided on the substrate or at least one of the sheets of glass. The substrate can also be flexible.

Moreover, the invention is a moisture detection system that includes a substrate, an electrical conductor disposed on the substrate, means for stimulating the electrical conductor with an oscillator signal, and means responsive to the oscillator signal and the electrical conductor for detecting changes in a resonant frequency of the electrical conductor in response to changes in an amount of moisture on the sheet adjacent the electrical conductor.

The substrate can be flexible and the system can further include a sheet in contact with the substrate. The system can also include a means for removing moisture from the sheet and means responsive to the detecting means for controlling when the removing means removes moisture from the substrate.

Lastly, the invention is a fluid level detection system that includes an electrically and magnetically nonconductive fluid reservoir having an electrical conductor disposed on the fluid reservoir. A means for stimulating stimulates the electrical conductor with an oscillator signal and a means responsive to the oscillator signal and the electrical conductor detects a change in a resonant frequency of the electrical conductor responsive to a change in level of fluid in the fluid reservoir and outputs a control signal when the detected change in the resonant frequency of the electrical conductor corresponds to less than a desired level of fluid in the fluid reservoir.

The electrical conductor can be disposed on a flexible substrate positioned on the fluid reservoir.

BRIEF DESCRIPTION OF THE DRAWINGS

FIG. 3 is a plan view of a sheet, such as a sheet of glass or a windshield, including a second embodiment of an antenna that includes a substrate having an electrical conductor disposed thereon for detecting moisture on the sheet;

FIG. 4 is a cross section taken along lines IV—IV in FIG. 3;

FIG. 5 is a cross section taken along lines V—V in FIG. 4;

DETAILED DESCRIPTION OF THE INVENTION

Figure 1:
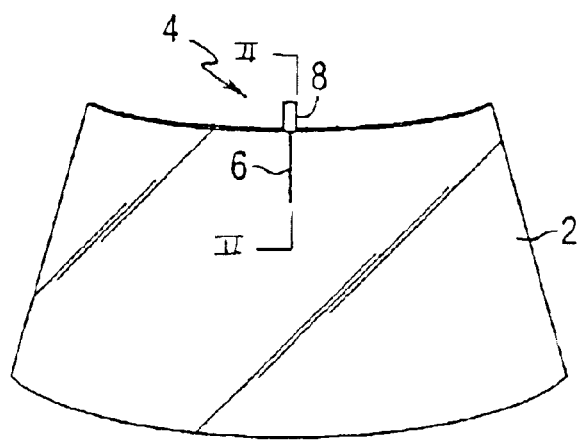
FIG. 1 is a plan view of a sheet, such as a sheet of glass or a windshield, including a first embodiment of an antenna having an electrical conductor that is utilized for detecting moisture on the sheet.

With reference to FIG. 1, a sheet or panel of optically transparent material, such as a sheet of glass or a vehicle windshield 2, includes an antenna 4 disposed thereon. A first embodiment of antenna 4 includes one or more electrical conductors 6 connected to a conductive foil 8 which is utilized for connecting electronic circuitry to electrical conductor 6. In the embodiment shown in FIG. 1, foil 8 is shown extending outside the periphery of windshield 2. However, this is not to be construed as limiting the invention since foil 8 may be disposed within the periphery of windshield 2.

Figure 2:
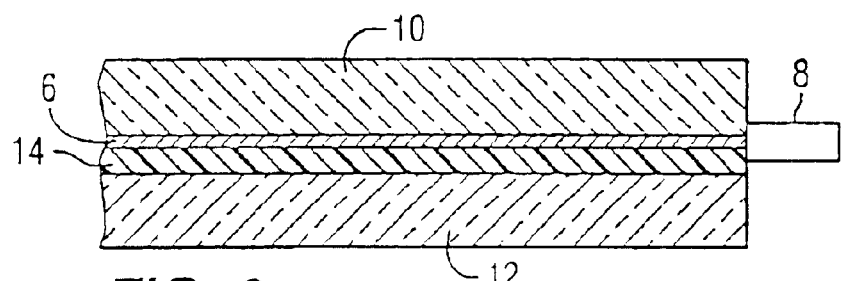
FIG. 2 is a cross section taken along lines II—II in FIG. 1.

With reference to FIG. 2, and with continuing reference to FIG. 1, windshield 2 is formed by outer and inner glass plies 10 and 12 bonded together by a plastic interlayer 14, such as polyvinylbutyral, to form windshield 2 as a unitary structure. Plies 10 and 12, however, may be other transparent rigid material, such as polycarbonate. Electrical conductor 6 can be disposed on an inward or an outward facing surface of glass ply 10 or glass ply 12. Electrical conductor 6 can be a conductive wire or sheet, a conductive coating applied to one of the surfaces of glass ply 10 or glass ply 12 in the form of a line or a sheet, or a dispersion of electrically conductive particles applied to one of the surfaces of glass ply 10 or glass ply 12 in the form of a line or a sheet. Desirably, electrical conductor 6 has a width and/or thickness that renders it essentially invisible to the naked eye.

With reference to FIGS. 3–5, a second embodiment of antenna 4 includes one or more electrical conductors 6 disposed on a flexible substrate 16. In FIGS. 3 and 4, part of flexible substrate 16 including electrical conductor 6 disposed thereon extends outside the periphery of windshield 2 to facilitate connection of electronic circuitry to electrical conductor 6. However, this is not to be construed as limiting the invention since flexible substrate 16 having electrical conductor 6 disposed thereon may be disposed entirely within the periphery of windshield 2.

As shown in FIG. 4, flexible substrate 16 can be sandwiched between glass plies 10 and 12 with electrical conductor 6 facing an inward facing surface of glass ply 10 or glass ply 12, or one of the outward facing surfaces of plastic interlayer 14. Alternatively, flexible substrate 16 can be disposed on an outward facing surface of glass ply 10 or glass ply 12 with electrical conductor 6 facing toward or away from said outward facing surface. To avoid undesirable exposure of flexible substrate 16 and/or electrical conductor 6, it is more desirable to sandwich flexible substrate 16 between glass plies 10 and 12 versus positioning flexible substrate 16 on an outward facing surface of glass ply 10 or glass ply 12.

Flexible substrate 16 can be formed from any suitable flexible and insulative material, such as polyethylene terephtalate, polyvinylbutyral, ultra-thin glass, etc. A desired pattern of electrical conductor 6 can be formed from a sheet of any suitable electrically conductive material adhered to flexible substrate 16 utilizing conventional photolithographic processing techniques. The desired pattern of electrical conductor 6 can also be formed on flexible substrate 16 by screen printing a suitable conductive material in the desired pattern on flexible substrate 16 or by ink jetting a suitable conductive material in the desired pattern on flexible substrate 16. The foregoing methods of forming the pattern of electrical conductor 6 on flexible substrate 16 are not to be construed as limiting the invention since the use of any suitable means for forming the desired pattern of electrical conductor 6 on flexible substrate 16 is envisioned.

Figure 6:
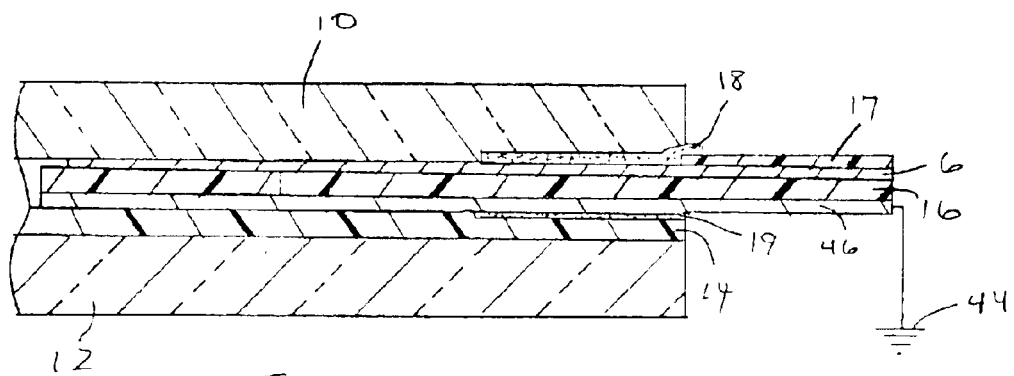
FIG. 6 is a cross section of the second embodiment antenna shown in FIG. 4 including a conductive material positioned on a side of the substrate opposite the electrical conductor.

With reference to FIGS. 5 and 6, and with continuing reference to FIGS. 3 and 4, the portion of flexible substrate 16 extending outside the periphery of windshield 2 can have electrical conductor 6 sandwiched between flexible substrate 16 and an insulative material 17 adhered to electrical conductor 6. Insulative material 17 can be formed from a sheet of suitable insulative material, such as Kapton® (a registered trademark of E. I. DuPont de Nemoirs and Company Corporation, Wilmington, Del.), or any other suitable solid or liquid insulative material that acts to protect electrical conductor 6. To avoid exposing the portion of electrical conductor 6 sandwiched between substrate 16 and insulative material 17 to moisture and/or particulate contaminates, an end of insulative material 17 terminates between glass plies 10 and 12.

To avoid exposure of electrical conductor 6 sandwiched between glass plies 10 and 12 to moisture and/or particulate contaminates, a thermoset adhesive 18 is disposed on the electrical conductor 6 side of flexible substrate 16 positioned between glass plies 10 and 12. This thermoset adhesive 18 covers the end of insulative material 17 sandwiched between glass plies 10 and 12 and extends between glass plies 10 and 12 a sufficient distance so that when it is cured, thermoset adhesive 18 forms with glass plies 10 and 12 and plastic interlayer 4 a hermetic seal that inhibits moisture and/or particulate contaminates from contacting the portion of electrical conductor 6 sandwiched between glass plies 10 and 12.

A pressure sensitive adhesive 19 can be sandwiched between flexible substrate 16 and plastic interlayer 14 for securing the position of flexible substrate 16 between glass plies 10 and 12 prior to exposing thermoset adhesive 18 and plastic interlayer 14 to a curing heat.

As shown in FIG. 5, flexible substrate 16 can include a ground conductor 7 that at least partially surrounds electrical conductor 6. Connecting ground conductor 7 to an external reference voltage 44, such as ground, forms a ground loop around electrical conductor 6. This ground loop avoids undesirable electromagnetic interference from affecting the operation of electrical conductor 6 acting in its capacity as a resonating element of antenna 4. Moreover, as shown in FIG. 6, a side of flexible substrate 16 opposite electrical conductor 6 can also or alternatively include a conductive material 46 disposed thereon that can be connected to external reference voltage 44. Conductive material 46 can be in the form of a sheet, one or more lines, a mesh, or any other suitable form that defines a faraday shield that avoids undesirable electromagnetic interference from affecting the operation of electrical conductor 6 acting in its capacity as a the resonating element of antenna 4.

Figure 7:
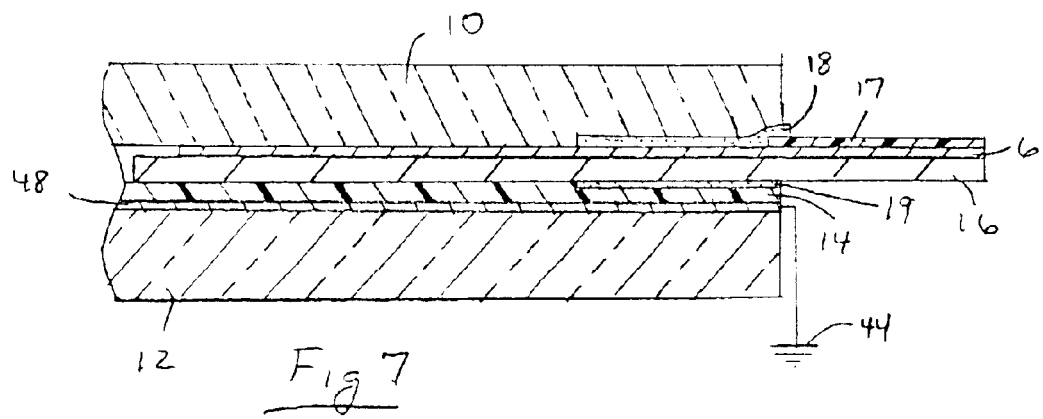
FIG. 7 is a cross section of the second embodiment antenna shown in FIG. 4 including an electrically conductive coating on the inside surface of one of the sheets of glass.

With reference to FIG. 7, and with continuing reference to FIGS. 3–6, an electrically conductive coating 48 can also or alternatively be formed on a surface, e.g., inner surface, of glass ply 12 and connected to reference voltage 44 for avoiding undesirable electromagnetic interference from affecting the operation of electrical conductor 6 acting in its capacity as the resonating element of antenna 4. Electrically conductive coating 48 can be transparent or colored. When colored, electrically conductive coating 48 can serve the dual purpose of a ground plane or faraday shield for antenna 4 and a sun shade of windshield 2. While described in connection with the second embodiment of antenna 4, it is to be appreciated that an electrically conductive coating 48 can also be disposed on a surface, e.g., inner surface, of glass ply 12 when utilized with the first embodiment antenna 4 shown in FIGS. 1 and 2. As can be seen, any one or a combination of ground conductor 7, conductive material 46 and/or electrically conductive coating 48 can be utilized for avoiding undesirable electromagnetic interference from affecting the operation of electrical conductor 6 acting in its capacity as the resonating element of antenna 4.

Figure 8:
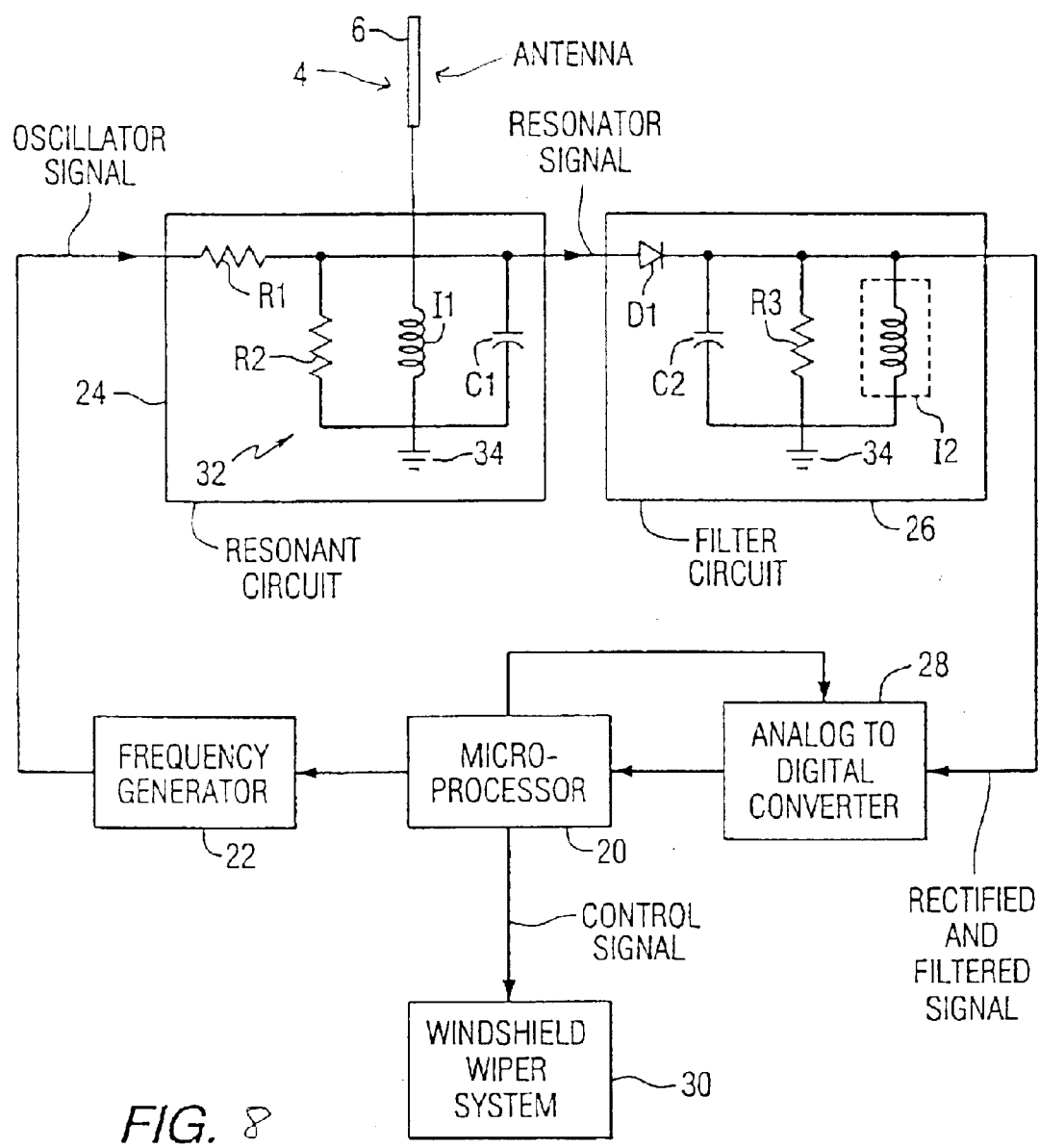
FIG. 8 is a schematic drawing of circuitry utilized to stimulate and detect the response of the electrical conductor of the first and second embodiment antennas.

With reference to FIG. 8, and with continuing reference to all previous figures, the electronic circuitry coupled to electrical conductor 6 of each embodiment of antenna 4 described above includes a microprocessor 20, a frequency generator 22, a resonant circuit 24, a filter circuit 26, and an analog-to-digital converter 28. A windshield wiper system 30 is connected to receive from microprocessor 20 one or more control signals which control the operation of windshield wiper system 30 in a manner to be described hereinafter.

Microprocessor 20 is interfaced with certain electronic hardware, such as ROM memory, RAM memory, I/O buffers, clock circuitry, and the like, which have not been included in FIG. 3 for simplicity of illustration. Microprocessor 20 operates under the control of a software program stored in a memory connected to microprocessor 20. Under the control of this software program, microprocessor 20 causes frequency generator 22 to output an oscillator signal having a predetermined amplitude and a predetermined frequency. This predetermined frequency can be between 300 kHz and 700 kHz and, more specifically, between 400 kHz and 600 kHz. The oscillator signal is supplied to resonant circuit 24 which is coupled to antenna 4. In response to receiving the oscillator signal, resonant circuit 24 outputs a resonator signal having an amplitude related to the resonant frequency of antenna 4.

Resonant circuit 24 includes a resistor R1 which isolates the oscillator signal from the resonator signal. Resonant circuit 24 also includes a tank circuit 32 connected between antenna 4 and a reference voltage 34, such as ground, on a side of resistor R1 opposite frequency generator 22. Tank circuit 32 can be configured to resonate at the predetermined frequency of the oscillator signal. Tank circuit 32 includes a resistor R2, an inductor I1 and a capacitor C1 connected in parallel between antenna 4 and reference voltage 34.

Filter circuit 26 includes a diode D1 connected to conduct the resonator signal from resonant circuit 24 toward analog-to-digital converter 28. A capacitor C2 and a resistor R3 are connected in parallel between a side of diode D1 opposite resonant circuit 24 and reference voltage 34. Optionally, an inductor 12 is connected in parallel with capacitor C2 and resistor R3. The output of filter circuit 26 is a rectified and filtered signal which is supplied to analog-to-digital converter 28. Under the control of microprocessor 20, analog-to-digital converter 28 samples the rectified and filtered signal and converts it into an equivalent digital signal which is sampled by microprocessor 20.

In order to detect the presence of moisture on windshield 2, microprocessor 20 causes frequency generator 22 to generate the oscillator signal when no moisture is present on an outward facing surface of windshield 2. Microprocessor 20 then determines the response of antenna 4 to the oscillator signal by sampling a first digital signal output by analog-to-digital converter 28 when antenna 4 is receiving the oscillator signal. Microprocessor 20 stores this first digital signal for future use.

Next, when moisture, e.g., condensed or diffused liquid such as water, is present on the outward facing surface of windshield 2, microprocessor 20 samples a second digital signal output by analog-to-digital converter 28 when antenna 4 is receiving the oscillator signal.

Alternatively, microprocessor 20 can sample the first digital signal when moisture e.g., condensed or diffused liquid such as water, is present on the outward facing surface of windshield 2 and can sample the second digital signal when no moisture is present on the outward facing surface of windshield 2. To this end, the first digital signal, corresponding to the presence or absence of moisture on windshield 2, can be utilized as the basis for determining from the second digital signal when moisture is present on or absent windshield 2. The use of the first and second digital signals to determine the presence or absence of moisture on windshield 2 will be described hereinafter.

It has been observed that the rectified and filtered signal output by filter circuit 26 has a different amplitude when moisture is present on windshield 2 adjacent antenna 4. More specifically, the rectified and filtered signal output by filter circuit 26 has an amplitude that increases or decreases to a limit with increasing moisture on windshield 2 adjacent antenna 4. For example, in the absence of moisture on windshield 2 adjacent antenna 4, the rectified and filtered signal has a first amplitude. However, when moisture in the form of droplets of water is received on windshield 2 adjacent antenna 4, the rectified and filtered signal output by filter circuit 26 has a second amplitude different than the first amplitude. Furthermore, when moisture in the form of diffused water is received on windshield 2 adjacent antenna 4, the rectified and filtered signal output by filter circuit 26 has a third amplitude different than the second amplitude.

This changing amplitude is caused by the impedance of antenna 4, at the predetermined frequency of the oscillator signal, changing in response to changes in the resonant frequency of antenna 4 due to increasing amounts of moisture on windshield 2 adjacent antenna 4. More specifically, the resonant frequency of antenna 4 increases in response to increasing moisture on windshield 2 adjacent antenna 4. Thus, for example, if the predetermined frequency of the oscillator signal is selected to equal the resonant frequency of antenna 4 when diffused liquid is present on windshield 2 adjacent antenna 4, when the amount of moisture on windshield 2 adjacent antenna 4 increases from no moisture to diffused liquid, the impedance of antenna 4 decreases whereupon the amplitude of the rectified and filtered signal output by filter circuit 26 decreases. Similarly, for example, if the predetermined frequency of the oscillator signal is selected to equal the resonant frequency of antenna 4 when no moisture is present on windshield 2 adjacent antenna 4, when the amount of moisture on windshield 2 adjacent antenna 4 increases from no moisture to diffused liquid, the impedance of antenna 4 increases whereupon the amplitude of the rectified and filtered signal output by filter circuit 26 increases. Thus, depending on relation of the predetermined frequency of the oscillator signal to the resonant frequency of antenna 4, the rectified and filtered signal output by filter circuit 26 can either increase or decrease in amplitude.

The electronic circuitry coupled to electrical conductor 6 can detect changes in the resonant frequency thereof due to changes in the moisture on windshield 2 adjacent conductor 6 between no moisture and diffused liquid. However, it has been observed that dew or mist on a surface of windshield 2 is best detected when electrical conductor 6 or substrate 16 is disposed in contact with the surface of windshield 2 receiving the dew or mist.

Next, microprocessor 20 compares the first digital signal to the second digital signal to determine the amount of moisture that is present on windshield 2 adjacent antenna 4. More specifically, microprocessor 20 takes the difference between the first and second digital signals and determines therefrom an amount of moisture that is present on windshield 2 adjacent antenna 4. Based on this determination, microprocessor 20 outputs a control signal to windshield wiper system 30 for controlling the operation thereof based on the amount of moisture on windshield 2.

Figure 9:
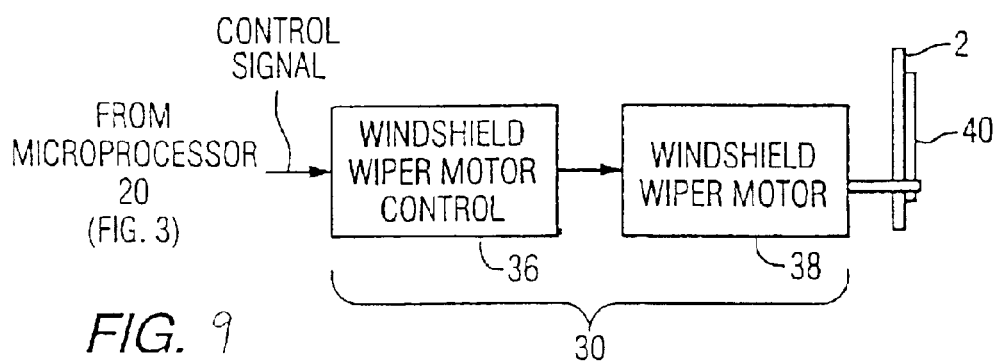
FIG. 9 is a schematic drawing of the windshield wiper system shown in FIG. 8.

With reference to FIG. 9, and with continuing reference to all previous figures, windshield wiper system 30 includes a windshield wiper motor control 36 which receives the control signal from microprocessor 20, and a windshield wiper motor 38 which is coupled to a windshield wiper blade 40 disposed on windshield 2. As discussed above, the control signal supplied by microprocessor 20 to windshield wiper motor control 36 is related to the difference between the first and second digital signals sampled by microprocessor 20. In order to control windshield wiper system 30 in accordance with the amount of moisture on windshield 2 adjacent antenna 4, the numerical range of digital difference values that can be processed by microprocessor 20 is divided into sections based on the desired control of windshield wiper system 30. For example, if the range of digital difference values is divided into two sections, the section corresponding to the upper numerical range of difference values corresponds to operating windshield wiper system 30 at a high speed while the lower numerical range of difference values corresponds to operating windshield wiper system 30 at a low speed. Thus, if a difference value between a current sample of the second digital signal and the first digital signal is within the upper numerical range of difference values, microprocessor 20 outputs the control signal which causes windshield wiper motor control 36 to control windshield wiper motor 38 to operate windshield wiper blade 40 at a high speed. Similarly, if the difference value between the current sample of the second digital signal and the first digital signal is within the lower numerical range of difference values, microprocessor 20 outputs the control signal which causes windshield wiper motor control 36 to control windshield wiper motor 38 to operate windshield wiper blade 40 at a low speed.

Various other modes of operation of windshield wiper system 30 can also be enabled by microprocessor 20 and windshield wiper motor control 36 as a function of the difference value between a current sample of the second digital signal and the first digital signal. These modes can include a single pulse mode where windshield wiper blade 40 is caused to wipe windshield 2 once, e.g., to remove dew or mist from windshield 2; a continuous duty cycle pulse mode, e.g., where there is a steady accumulation of water droplets on windshield 2, but the accumulation is not sufficient enough to warrant operation of windshield wiper system 30 at the low speed; and a variable duty cycle pulse mode where wiping of windshield 2 by windshield wiper blade 40 varies as a function of the amount and/or rate of moisture accumulation on windshield 2.

Microprocessor 20 can be configured to output two or more different control signals which cause windshield wiper system 30 to implement two or more of the above modes of operation in response to varying amounts of moisture on windshield 2. In the absence of moisture on windshield 2, microprocessor 20 can cause windshield wiper system 30 to either discontinue or not initiate the wiping of windshield 2 with windshield wiper blade 40.

Figure 10A:
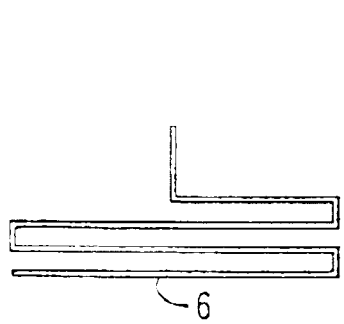
FIGS. 10a–10d show alternate embodiments of the electrical conductor of the first and second embodiment antennas.
Figure 10B:
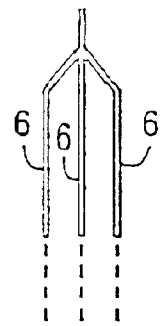
Figure 10C:
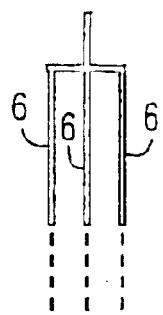
Figure 10D:
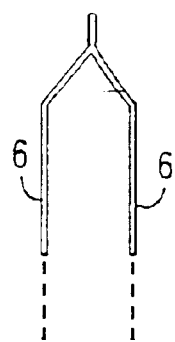

With reference to FIGS. 10a–10d, various different embodiments of electrical conductor 6 of the first and second embodiment antennas 4 are illustrated. FIG. 10a and FIG. 5 show electrical conductor 6 formed in a serpentine pattern. FIGS. 10b and 10c show three parallel electrical conductors 6 extending in spaced relation from a common junction. As indicated by the dashed extensions of electrical conductors 6 in FIGS. 10b and 10c, electrical conductors 6 can be formed to any desired length. Lastly, in FIG. 10d, two parallel electrical conductors 6 extend in spaced relation from a common junction. Again, the dash lines extending from electrical conductors 6 in FIG. 10d indicate that electrical conductors 6 can have any desired length.

The present invention has several advantages over prior art systems for detecting moisture. These advantages include antenna 4 being essentially invisible to the naked eye from about one meter; antenna 4 can be disposed in a clear or nontransparent part of windshield 2; antenna 4 is not sensitive to dirt; antenna 4 can detect the presence of moisture over a larger area than prior art sensors of comparable size; antenna 4 is useful with substrates of various thickness and composition; and the present invention can detect the presence of moisture droplets of smaller size, e.g., dew or mist, on windshield 2 than the prior art systems for detecting moisture.

Figure 11:
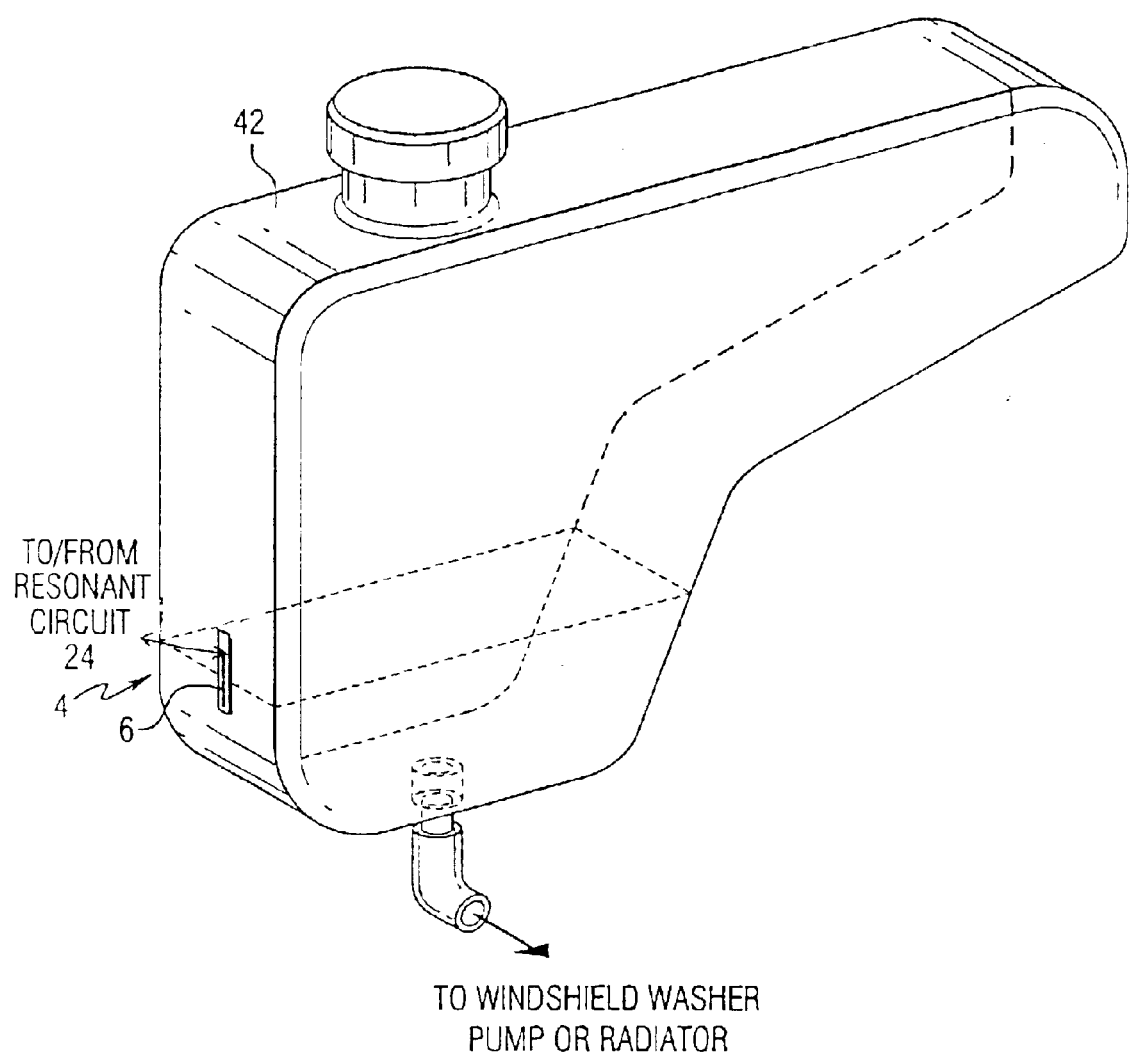
FIG. 11 is an isolated perspective view of a fluid reservoir for a vehicle including the electrical conductor of the first and second embodiment antenna disposed thereon.

With reference to FIG. 11 and with reference back to FIG. 8, the present invention can also be utilized to detect a level of one or more fluids, such as the level of a fluid in a vehicle. Specifically, antenna 4 can be mounted on an electrically and magnetically nonconductive fluid reservoir 42. Preferably, antenna 4 is mounted on an exterior of fluid reservoir 42 adjacent a lower end thereof. However, this is not to be construed as limiting the invention. Fluid reservoir 42 can be configured to receive windshield washer fluid, radiator fluid, or any other fluid utilized by a vehicle, the level of which fluid can be measured utilizing antenna 4 and the electronic circuitry shown in FIG. 8.

In order to detect the level of fluid in fluid reservoir 42, the oscillator signal is supplied to electrical conductor 6 of antenna 4 when no fluid is received in fluid reservoir 42. A first response of electrical conductor 6 is sampled and stored for later use. At suitable times when fluid is received in the fluid reservoir, plural second responses of electrical conductor 6 to the oscillator signal are sampled. Each second response is compared to the first response. When a second response has a predetermined relation to the first response, the electronic circuitry outputs a corresponding control signal which activates a suitable indicator, e.g., "check washer fluid", "check radiator fluid", etc.

It is to be appreciated that decreasing the fluid level in fluid reservoir 42 decreases the difference between the first response and the second response of antenna 4. Thus, when the second response has the predetermined relation to the first response indicative of the fluid level decreasing to a predetermined level, the electronic circuitry outputs the control signal. To facilitate detecting the change in the resonant frequency of antenna 4, the predetermined frequency of the oscillator signal can be selected to optimize the change in impedance of antenna 4 in response to the presence of fluid in fluid reservoir 42. Similar comments apply in respect of the change in resonant frequency of antenna 4 due to the presence of moisture on windshield 2.

When a vehicle includes multiple antenna 4, a multiplexer (not shown) can be connected between each antenna 4 and the electronic circuitry shown in FIG. 8. Under the control of microprocessor 20, the multiplexer can selectively connect the electronic circuitry to each antenna 4 for supplying the oscillator signal at an appropriate frequency to each antenna 4 and for detecting the response of each antenna 4 to the supplied oscillator signal. Preferably, under the control of the software program, microprocessor 20 can adjust the frequency of the oscillator signal output by frequency generator 22 to optimize the change in the resonant frequency of each antenna 4 to detect the presence or absence of a particular fluid.

The invention has been described with reference to the preferred embodiments. Obvious modifications and alterations will occur to others upon reading and understanding the preceding detailed description. For example, while described in connection with the detection of moisture on windshield 2, the present invention can also be utilized to detect moisture on surfaces of rigid or flexible substrates utilized in connection with other applications. Similarly, while described in connection with detection of fluid levels in a fluid reservoir 42 mounted on a vehicle, the present invention can also be utilized to detect the level of a fluid received in a fluid reservoir utilized in other applications. Moreover, while described in connection with the control of windshield wiper system 30, microprocessor 20 can also be utilized to control a vehicle headlamp system, a vehicle windshield dehumidification system and/or any other vehicle or non-vehicle based system that it is desired to control as a function of the presence of moisture on a substrate. Still further, while the various components of the electronic circuitry are preferably connected by conductors, it should be appreciated that suitable signals can be conveyed between two or more of these components via suitable radio frequency (RF) and/or optical signal means. Lastly, microprocessor 20 can also be configured to record for subsequent retrieval and display, the days when moisture is detected on a substrate and/or the extent of operation of windshield wiper system 30. This information can then be used for information purposes, e.g., to determine the number of days in a month it rains, and/or to estimate when blades of the windshield wiper system 30 may require replacement. It is intended that the invention be construed as including all such modifications and alterations insofar as they come within the scope of the appended claims or the equivalents thereof.

What is claimed is:

1. A moisture detection system comprising:
an electrical conductor disposed on a surface of a substrate and having a resonant frequency that varies as a function of an amount of moisture present adjacent the electrical conductor;
an oscillator which outputs an oscillator signal at a predetermined amplitude and a predetermined frequency;
a resonator circuit coupled to the electrical conductor and responsive to the oscillator signal for outputting a resonator signal having an amplitude related to the resonant frequency of the electrical conductor;
a filter circuit responsive to the resonator signal for outputting a rectified and filtered signal;
an analog-to-digital converter responsive to the rectified and filtered signal for outputting a digital signal related to the rectified and filtered signal; and
a controller responsive to the digital signal for causing another system to operate in accordance with the digital signal.

2. The system as set forth in claim 1, wherein the other system is a wiper system that is responsive to the controller for adjusting a rate moisture is removed from adjacent the electrical conductor as a function of an amount of moisture present adjacent the electrical conductor and/or a rate moisture accumulates adjacent the electrical conductor.

3. The system as set forth in claim 2, wherein:
the wiper system includes a means for wiping; and
the wiper system is responsive to the digital signal for causing the wiping means to remove moisture from a surface.

4. A moisture detection system comprising:
an electrical conductor disposed on a surface of a substrate and having a resonant frequency that varies as a function of an amount of moisture present adjacent the electrical conductor;
an oscillator which outputs an oscillator signal at a predetermined amplitude and a predetermined frequency;
a resonator circuit coupled to the electrical conductor and responsive to the oscillator signal for outputting a resonator signal having an amplitude related to the resonant frequency of the electrical conductor;
a filter circuit responsive to the resonator signal for outputting a rectified and filtered signal;
an analog-to-digital converter responsive to the rectified and filtered signal for outputting a digital signal related to the rectified and filtered signal; and
a controller responsive to the digital signal for causing another system to operate in accordance with the digital signal, wherein the predetermined frequency is between one of (i) 300 and 700 kHz and (ii) 400 and 600 kHz.

5. The system as set forth in claim 1, wherein:
the substrate is a vehicle windshield having a plurality of transparent sheets laminated together, and
the electrical conductor is sandwiched between the sheets.

6. The system as set forth in claim 1, wherein the substrate is a flexible substrate.

7. The system as set forth in claim 6, further including a vehicle windshield having a plurality of transparent sheets laminated together with the flexible substrate sandwiched between the transparent sheets.

8. The system as set forth in claim 7, further including an electrically conductive coating disposed on a surface of at least one transparent sheet.

9. The system as set forth in claim 8, wherein said surface is positioned on a side of the flexible substrate opposite the electrical conductor.

10. A moisture detection system comprising:
an electrical conductor disposed on a surface of a substrate and having a resonant frequency that varies as a function of an amount of moisture present adjacent the electrical conductor;
an oscillator which outputs an oscillator signal at a predetermined amplitude and a predetermined frequency;
a resonator circuit coupled to the electrical conductor and responsive to the oscillator signal for outputting a resonator signal having an amplitude related to the resonant frequency of the electrical conductor;
a filter circuit responsive to the resonator signal for outputting a rectified and filtered signal;
an analog-to-digital converter responsive to the rectified and filtered signal for outputting a digital signal related to the rectified and filtered signal; and
a controller responsive to the digital signal for causing another system to operate in accordance with the digital signal, wherein:
the substrate is a flexible substrate; and
the flexible substrate further includes at least one of (i) a ground conductor disposed on the flexible substrate at least partially surrounding the electrical conductor and (ii) a conductive material disposed on a surface of the flexible substrate opposite the electrical conductor, said conductive material having a form that defines a faraday shield.

11. The system as set forth in claim 1, wherein the resonator circuit includes:
a tank circuit having a capacitor and an inductor connected in parallel between the electrical conductor and a reference voltage; and
a resistor connected between the oscillator and the electrical conductor side of the tank circuit.

12. A moisture detection system comprising:
an electrical conductor disposed on a surface of a substrate and having a resonant frequency that varies as a function of an amount of moisture present adjacent the electrical conductor;
an oscillator which outputs an oscillator signal at a predetermined amplitude and a predetermined frequency;
a resonator circuit coupled to the electrical conductor and responsive to the oscillator signal for outputting a resonator signal having an amplitude related to the resonant frequency of the electrical conductor;
a filter circuit responsive to the resonator signal for outputting a rectified and filtered signal;
an analog-to-digital converter responsive to the rectified and filtered signal for outputting a digital signal related to the rectified and filtered signal; and
a controller responsive to the digital signal for causing another system to operate in accordance with the digital signal, wherein the filter circuit includes:
a diode connected to conduct current from the resonator toward the analog-to-digital converter; and
a capacitor connected between an end of the diode adjacent the analog-to-digital converter and a reference voltage.

13. A moisture detector system comprising:
means disposed on a substrate for conducting electrical current, the conducting means having a resonant frequency that changes as a function of moisture adjacent the conducting means;
an oscillator for outputting to the conducting means an oscillator signal having a predetermined frequency and a first amplitude;
means responsive to the oscillator signal for outputting a resonator signal having a second amplitude related to the resonant frequency of the conducting means, wherein the second amplitude is different than the first amplitude; and
means responsive to the resonator signal for outputting a control signal having a value related to the second amplitude of the resonator signal.

14. The moisture detector as set forth in claim 13, further including a wiper system responsive to the control signal for wiping moisture from adjacent the conducting means based on an amount of moisture adjacent the conducting means and/or a rate moisture accumulates adjacent the conducting means.

15. A moisture detector system comprising:
means disposed on a substrate for conducting electrical current, the conducting means having a resonant frequency that changes as a function of moisture adjacent the conducting means;
an oscillator for outputting to the conducting means an oscillator signal having a predetermined frequency and a first amplitude;
means responsive to the oscillator signal for outputting a resonator signal having a second amplitude related to the resonant frequency of the conducting means, wherein the second amplitude is different than the first amplitude; and
means responsive to the resonator signal for outputting a control signal having a value related to the second amplitude of the resonator signal, wherein the conducting means includes at least one of (i) one or more lines of conductive material, (ii) one or more sheets of conductive material, and (iii) a dispersion of conductive particles in the form of one or more lines and/or sheets.

16. A moisture detector system comprising:
means disposed on a substrate for conducting electrical current, the conducting means having a resonant frequency that changes as a function of moisture adjacent the conducting means;
an oscillator for outputting to the conducting means an oscillator signal having a predetermined frequency and a first amplitude:
means responsive to the oscillator signal for outputting a resonator signal having a second amplitude related to the resonant frequency of the conducting means, wherein the second amplitude is different than the first amplitude; and
means responsive to the resonator signal for outputting a control signal having a value related to the second amplitude of the resonator signal, wherein the substrate is a windshield that includes plural sheets of glass laminated together.

17. The moisture detector as set forth in claim 16, wherein the conducting means is sandwiched between the sheets of glass.

18. A moisture detector system comprising:
means disposed on a substrate for conducting electrical current, the conducting means having a resonant frequency that changes as a function of moisture adjacent the conducting means;
an oscillator for outputting to the conducting means an oscillator signal having a predetermined frequency and a first amplitude;
means responsive to the oscillator signal for outputting a resonator signal having a second amplitude related to the resonant frequency of the conducting means, wherein the second amplitude is different than the first amplitude; and
means responsive to the resonator signal for outputting a control signal having a value related to the second amplitude of the resonator signal, wherein:
the substrate is a flexible substrate that is coupled to a sheet; and
the conducting means has a resonant frequency that changes as a function of moisture on the sheet.

19. The moisture detector as set forth in claim 18, further including a wiper system disposed in operative relation to the sheet and responsive to the control signal for wiping the sheet based on an amount of moisture on the sheet and/or a rate moisture accumulates on the sheet.

20. The moisture detector as set forth in claim 18, wherein the conducting means includes one or more lines of electrically conductive material disposed on the flexible substrate.

21. The moisture detector as set forth in claim 18, wherein the sheet is a windshield that includes plural sheets of glass laminated together.

22. The moisture detector as set forth in claim 21, wherein the flexible substrate is sandwiched between the sheets of glass.

23. The moisture detector as set forth in claim 18, wherein the flexible substrate further includes at least one of (i) a ground conductor disposed on the flexible substrate at least partially surrounding the conducting means and (ii) a conductive material disposed on a surface of the flexible substrate opposite the conducting means, said conductive material having a form that defines a faraday shield.

24. The moisture detector as set forth in claim 21, further including an electrically conductive coating disposed on a surface of at least one sheet.

25. The moisture detector as set forth in claim 24, wherein said surface is positioned on a side of the flexible substrate opposite the conducting means.

26. A method of moisture detection comprising:
(a) providing a substrate having an electrical conductor disposed thereon;
(b) stimulating the electrical conductor with an oscillator signal in the absence of moisture adjacent the electrical conductor;
(c) determining a first amplitude of the electrical conductor to the stimulation in step (b);
(d) stimulating the electrical conductor with the oscillator signal when moisture is present adjacent the electrical conductor;
(e) determining a second amplitude of the electrical conductor to the stimulation in step (d), wherein the second amplitude is different than the first amplitude due to a change in resonant frequency of the electrical conductor in response to the presence of moisture adjacent the electrical conductor; and
(f) determining a difference between the first amplitude and the second amplitude, wherein the difference is related to the amount of moisture present adjacent the electrical conductor.

27. The method as set forth in claim 26, further including removing moisture from adjacent the electrical conductor at a rate related to the difference between the first amplitude and the second amplitude.

28. The method as set forth in claim 26, further including sandwiching the substrate between at least two sheets of glass.

29. The method as set forth in claim 28, further including providing shielding means on at least one of (i) the substrate and (ii) at least one of the sheets of glass.

30. The method as set forth in claim 28, wherein the substrate is flexible.

31. A moisture detection system comprising: a substrate; an electrical conductor disposed on the substrate; means for stimulating the electrical conductor with an oscillator signal operating at a predetermined frequency; means responsive to the oscillator signal and the electrical conductor for detecting changes in resonant frequency of the electrical conductor in response to changes in an amount of moisture disposed adjacent the electrical conductor; and a controller responsive to the frequency changes for causing another system to operate in accordance with the changes.

32. The system as set forth in claim 31, wherein the substrate is flexible.

33. A moisture detection system comprising: a substrate; an electrical conductor disposed on the substrate; means for stimulating the electrical conductor with an oscillator signal; means responsive to the oscillator signal and the electrical conductor for detecting changes in a resonant frequency of the electrical conductor in response to changes in an amount of moisture disposed adjacent the electrical conductor; a controller responsive to the frequency changes for causing another system to operate in accordance with the changes; and a sheet in contact with the substrate.

34. The system as set forth in claim 33, further including:
means for removing an accumulation of moisture on the sheet; and
means responsive to the detecting means for controlling when the removing means removes the accumulation of moisture from the sheet.

35. The system as set forth in claim 34, wherein the substrate is disposed on one of (i) a side of the sheet receiving the accumulation of moisture and (ii) a side of the sheet not receiving the accumulation of moisture.

36. The system as set forth in claim 33, wherein the sheet is formed from a plurality of sheets joined together.

37. A moisture detection system comprising: a fluid reservoir, an electrical conductor disposed on the fluid reservoir; means for stimulating the electrical conductor with an oscillator signal; means for stimulating the electrical conductor with an oscillator signal; means responsive to the oscillator signal and the electrical conductor for detecting a change in a resonant frequency of the electrical conductor responsive to a change in a level of fluid in the fluid reservoir and for outputting a control signal when the detected change in the resonant frequency of the electrical conductor corresponds to less than a desired level of fluid in the fluid reservoir; and a controller responsive to the frequency changes for causing another system to operate in accordance with the changes.

38. The moisture detection system of claim 37, wherein the electrical conductor is disposed on a flexible substrate positioned on the fluid reservoir.

* * * * *